(12) United States Patent
Girouard et al.

(10) Patent No.: US 7,158,824 B2
(45) Date of Patent: Jan. 2, 2007

(54) STRESS REDUCTION PACING FOR ARTERIAL PLAQUE STABILIZATION

(75) Inventors: Steven D. Girouard, Woodbury, MN (US); Bruce H. KenKnight, Maple Grove, MN (US); Joseph M. Pastore, Minneapolis, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 447 days.

(21) Appl. No.: 10/664,410

(22) Filed: Sep. 16, 2003

(65) Prior Publication Data

US 2004/0116970 A1 Jun. 17, 2004

Related U.S. Application Data

(63) Continuation-in-part of application No. 10/298,156, filed on Nov. 15, 2002, now Pat. No. 7,065,405.

(51) Int. Cl.
*A61N 1/36* (2006.01)

(52) U.S. Cl. .......................................................... 607/2

(58) Field of Classification Search ................ None
See application file for complete search history.

(56) References Cited

U.S. PATENT DOCUMENTS

| | | | |
|---|---|---|---|
| 4,549,548 A | 10/1985 | Wittkampf et al. | |
| 4,628,934 A | 12/1986 | Pohndorf et al. | |
| 5,174,289 A | 12/1992 | Cohen | |
| 5,267,560 A | 12/1993 | Cohen | |
| 5,366,443 A * | 11/1994 | Eggers et al. ............... | 604/114 |
| 5,935,160 A | 8/1999 | Auricchio et al. | |
| 5,995,871 A | 11/1999 | Knisley | |
| 6,201,991 B1 * | 3/2001 | Chekanov ...................... | 607/2 |
| 6,628,988 B1 * | 9/2003 | Kramer et al. ................. | 607/9 |
| 7,065,405 B1 | 6/2006 | Pastore et al. | |
| 2002/0045809 A1 * | 4/2002 | Ben-Haim ................... | 600/374 |
| 2002/0161410 A1 | 10/2002 | Kramer et al. | |
| 2003/0036773 A1 * | 2/2003 | Whitehurst et al. ............ | 607/3 |
| 2004/0054381 A1 | 3/2004 | Pastore et al. | |

OTHER PUBLICATIONS

Barbone, Alessandro, "Comparison of right and left ventricular responses to left ventricular assist device support in patients with sever heart failure: a primary role of mechanical unloading underlying reverse remodeling", *Circulation*, 104(6), (Aug. 7, 2001), 670-675.

Heerdt, Paul M., "Chronic Unloading By Left Ventricular Assist Device Reverses Contractile Dysfunction and Alters Gene Expression in End-Stage Heart Failure", *Circulation*, 102(22), (Nov. 28, 2000), 2713-2719.

Prinzen, Frits W., "Mapping of regional myocardial strain and work during ventricular pacing: experimental study using magnetic resonance imaging tagging", *Journal of the American College of Cardiology*, 33(6), (May 1999), 1735-1742.

* cited by examiner

*Primary Examiner*—Carl Layno
(74) *Attorney, Agent, or Firm*—Schwegman, Lundberg, Woessner, & Kluth, P.A.

(57) ABSTRACT

A method for stabilizing atherosclerotic plaque with the intra-myocardial portion of a coronary artery is presented. Pacing therapy is utilized to pre-excite ventricular myocardium near the site of a plaque and thereby mechanically unload the myocardial region. Such mechanical unloading results in less deforming stress being transmitted to the plaque during ventricular systole.

17 Claims, 2 Drawing Sheets

STRESS REDUCTION PACING FOR ARTERIAL PLAQUE STABILIZATION

CROSS-REFERENCE TO RELATED APPLICATION(S)

"This application is a continuation-in-part of U.S. patent application Ser. No. 10/298,156, filed on Nov. 15, 2002, now U.S. Pat. No. 7,065,405, the specification of which is incorporated herein by reference."

FIELD OF THE INVENTION

This invention pertains to apparatus and methods for the diagnosis and treatment of heart disease and to devices providing electrostimulation to the heart such as cardiac pacemakers.

BACKGROUND

Myocardial infarctions, or heart attacks, are one of the commonest causes of serious illness and death in Western countries. The coronary arteries, which supply the heart with oxygen and nutrients, may become diseased with atherosclerosis that reduces blood flow. Atherosclerotic plaque within the artery may lead to the clotting of blood (thrombosis) in the artery, and this can cause sudden, complete obstruction and result in damage to a substantial area of heart tissue. This may end in sudden death, usually due to abnormal heart rhythm that prevents effective pumping.

An atherosclerotic plaque is the site of an inflammatory reaction within the wall of an artery. The plaque is made up of a core containing lipid and inflammatory cells surrounded by a connective tissue capsule. The portion of the capsule facing the arterial lumen is called the plaque cap. Atherosclerotic plaque rupture is the primary mechanism which leads to thrombus formation. When the plaque ruptures, the plaque cap tears to expose the lipid core to blood in the arterial lumen. The core area is highly thrombogenic, containing tissue factor, fragments of collagen, and crystalline surfaces to accelerate coagulation. The exposed collagen triggers platelets to adhere to the site. The aggregated platelets then initiate the blood clotting cascade and cause a thrombus to form. Thrombus forms initially in the plaque itself and is then expanded and distorted from within so that it extends into the arterial lumen. Certain atherosclerotic plaques, termed vulnerable plaques, are at greater risk of rupture than others. Such vulnerable plaques are characterized by, among other things, a large core, a thin cap, and a large number of inflammatory cells.

Plaque rupture is the result of enhanced inflammatory activity within the plaque which can be triggered by physical and chemical stresses. Portions of the coronary arteries which are surrounded by the ventricular myocardium are subjected to mechanical stresses when the ventricles contract during systole. Vulnerable plaques located in the intramyocardial portions of coronary arteries may thus be at great risk for rupture.

SUMMARY OF THE INVENTION

In accordance with the present invention, multi-site pacing is used to change the distribution of wall stress experienced by certain regions of the ventricles during systole in order to mechanically unload those regions and thereby transmit less deforming force to atherosclerotic plaque sites in the intra-myocardial vasculature of the regions. After identification of sites of atherosclerotic plaque in a patient's coronary arteries, corresponding pacing sites located in proximity thereto are selected. An implanted cardiac rhythm management device may then be configured with pacing electrodes disposed at such sites and programmed to deliver stress reduction pacing therapy.

DETAILED DESCRIPTION

Figure 1:
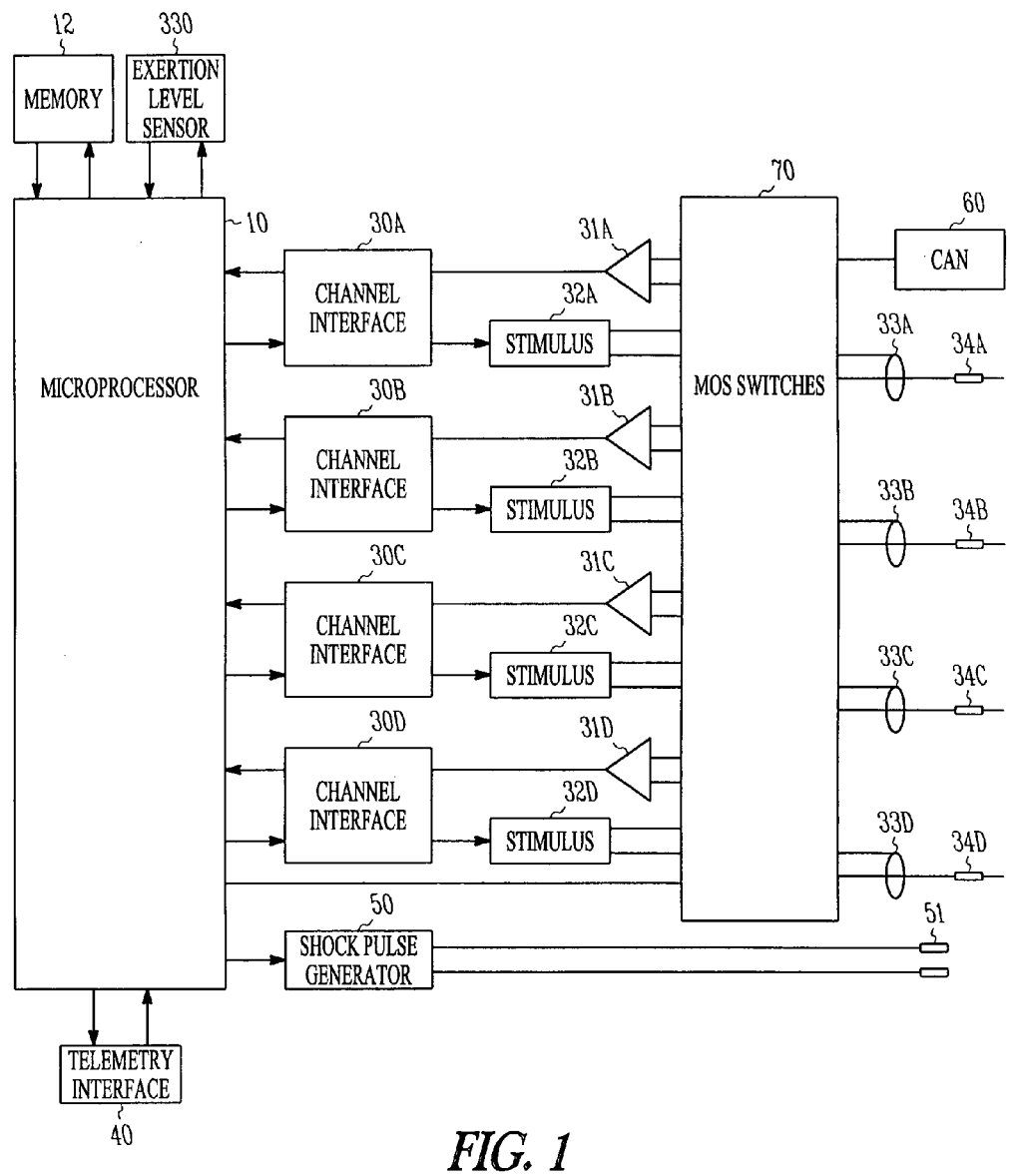
FIG. 1 is a block diagram of an exemplary cardiac rhythm management device for practicing the present invention.

During ventricular systole, the ventricular myocardium contracts in order to raise intra-ventricular pressure and eject blood from the ventricles. As the myofibrils in the ventricular walls shorten, the intra-myocardial portions of the coronary arteries within the ventricular walls are thereby subjected to deforming forces. Such deforming forces have the potential to mechanically destabilize intravascular atherosclerotic plaque in those arteries, leading to thrombosis and a myocardial infarction. The present invention utilizes pacing therapy to mechanically unload regions of the ventricular myocardium containing arteries with intravascular plaque and thereby subject those arteries to lessened deforming forces during systole.

1. Pre-Excitation Pacing Therapy

One example of pre-excitation pacing therapy for the purpose of improving cardiac function is cardiac resynchronization therapy (CRT). In ventricular resynchronization therapy, the ventricles are paced at more than one site in order to affect a spread of excitation that results in a more coordinated contraction and thereby overcome interventricular or intraventricular conduction defects. Biventricular pacing is one example of resynchronization therapy in which both ventricles are paced in order to synchronize their respective contractions. Resynchronization therapy may also involve multi-site pacing applied to only one chamber. For example, a ventricle may be paced at multiple sites with excitatory stimulation pulses in order to produce multiple waves of depolarization that emanate from the pacing sites. This may produce a more coordinated contraction of the ventricle and thereby compensate for intraventricular conduction defects that may exist.

Pacing therapy may also be employed for the purpose of redistributing the stresses to which regions of the myocardium are subjected during systole. The degree to which a heart muscle fiber is stretched before it contracts is termed the preload. In normal myocardium, the maximum tension and velocity of shortening of a muscle fiber increases with increasing preload. The increase in contractile response of the heart with increasing preload is known as the Frank-Starling principle. When a myocardial region contracts late relative to other regions, the earlier contraction of opposing regions stretches the later contracting region and increases its preload. The degree of tension or stress on a heart muscle fiber as it contracts is termed the afterload. Because pressure within the ventricles rises rapidly from a diastolic to a systolic value as blood is pumped out into the aorta and pulmonary arteries, the part of the ventricle that first contracts does so against a lower afterload than does a part of the ventricle contracting later. Thus, a myocardial region that contracts earlier than other regions during systole is subjected to both a decreased preload and a decreased afterload. What is referred to herein as stress reduction pacing makes use of this phenomena in order to redistribute myocardial wall stress during systole by pacing one or more sites in a ventricle with one or more pacing pulses delivered in a specified pulse output sequence. The pace or paces are delivered in a manner that excites a region of the myocardium receiving a pace earlier during systole than other regions so that it experiences less afterload and preload. This pre-excitation of the myocardial region relative to other regions unloads the region from mechanical stress. Pacing sites for stress reduction pacing may be selected in such a manner that previously stressed myocardial regions are pre-excited and hence experience lessened mechanical wall stress during systole. Pre-excitation of previously stressed regions may be effective in preventing or reversing cardiac remodeling.

In accordance with the present invention, one or more pacing sites for pre-excitation are selected as regions of the ventricular myocardium containing arteries with intravascular plaque. Pre-excitation of those regions mechanically unloads them during systole, thereby transmitting less deforming forces to the intra-myocardial vasculature within the region. An increased preload and afterload also requires increased energy expenditure by the ventricular myocardium which, in turn, increases its perfusion requirements. Pre-excitation of a myocardial region may thus also reduce local blood flow in the region and thereby subject the intravascular plaque in the region to less shear force caused by flowing blood.

2. Hardware Platform

Cardiac rhythm management devices such as pacemakers are usually implanted subcutaneously on a patient's chest and have leads threaded intravenously into the heart to connect the device to electrodes used for sensing and pacing. A programmable electronic controller causes the pacing pulses to be output in response to lapsed time intervals and sensed electrical activity (i.e., intrinsic heart beats not as a result of a pacing pulse). Pacemakers sense intrinsic cardiac electrical activity by means of internal electrodes placed near the chamber to be sensed. A depolarization wave associated with an intrinsic contraction of the atria or ventricles that is detected by the pacemaker is referred to as an atrial sense or ventricular sense, respectively. In order to cause such a contraction in the absence of an intrinsic beat, a pacing pulse (either an atrial pace or a ventricular pace) with energy above a certain pacing threshold is delivered to the chamber.

FIG. 1 shows a system diagram of a microprocessor-based cardiac rhythm management device or pacemaker suitable for practicing the present invention. The device is equipped with multiple sensing and pacing channels which may be physically configured to sense and/or pace multiple sites in the atria or the ventricles. The controller 10 of the pacemaker is a microprocessor which communicates with a memory 12 via a bidirectional data bus. The memory 12 typically comprises a ROM (read-only memory) for program storage and a RAM (random-access memory) for data storage. The controller could be implemented by other types of logic circuitry (e.g., discrete components or programmable logic arrays) using a state machine type of design, but a microprocessor-based system is preferable. As used herein, the term "circuitry" should be taken to refer to either discrete logic circuitry or to the programming of a microprocessor.

Shown in the figure are four exemplary sensing and pacing channels designated "a" through "d" comprising bipolar leads with ring electrodes 34a–d and tip electrodes 33a–d, sensing amplifiers 31a–d, pulse generators 32a–d, and channel interfaces 30a–d. Each channel thus includes a pacing channel made up of the pulse generator connected to the electrode and a sensing channel made up of the sense amplifier connected to the electrode. The channel interfaces 30a–d communicate bidirectionally with microprocessor 10, and each interface may include analog-to-digital converters for digitizing sensing signal inputs from the sensing amplifiers and registers that can be written to by the microprocessor in order to output pacing pulses, change the pacing pulse amplitude, and adjust the gain and threshold values for the sensing amplifiers. The sensing circuitry of the pacemaker detects a chamber sense, either an atrial sense or ventricular sense, when an electrogram signal (i.e., a voltage sensed by an electrode representing cardiac electrical activity) generated by a particular channel exceeds a specified detection threshold. Pacing algorithms used in particular pacing modes employ such senses to trigger or inhibit pacing, and the intrinsic atrial and/or ventricular rates can be detected by measuring the time intervals between atrial and ventricular senses, respectively.

The electrodes of each bipolar lead are connected via conductors within the lead to a MOS switching network 70 controlled by the microprocessor. The switching network is used to switch the electrodes to the input of a sense amplifier in order to detect intrinsic cardiac activity and to the output of a pulse generator in order to deliver a pacing pulse. The switching network enables the device to sense or pace either in a bipolar mode using both the ring and tip electrodes of a lead or in a unipolar mode using only one of the electrodes of the lead with the device housing or can 60 serving as a ground electrode. One way in which the device may alter the spatial distribution of pacing is to switch from unipolar to bipolar pacing (or vice-versa) or to interchange which electrodes of a bipolar lead are the cathode and anode during bipolar pacing. A shock pulse generator 50 is also interfaced to the controller for delivering a cardioversion/defibrillation shock via a pair of shock electrodes 51 to the atria or ventricles upon detection of a shockable tachyarrhythmia.

The controller 10 controls the overall operation of the device in accordance with programmed instructions stored in memory, including controlling the delivery of paces via the pacing channels, interpreting sense signals received from the sensing channels, and implementing timers for defining escape intervals and sensory refractory periods. An exertion level sensor 330 (e.g., an accelerometer, a minute ventilation sensor, or other sensor that measures a parameter related to metabolic demand) enables the controller to adapt the pacing rate in accordance with changes in the patient's physical activity. A telemetry interface 40 is also provided which enables the controller to communicate with an external programmer.

The controller is capable of operating the device in a number of programmed pacing modes which define how pulses are output in response to sensed events and expiration of time intervals. Most pacemakers for treating bradycardia are programmed to operate synchronously in a so-called demand mode where sensed cardiac events occurring within a defined interval either trigger or inhibit a pacing pulse. Inhibited demand pacing modes utilize escape intervals to control pacing in accordance with sensed intrinsic activity such that a pacing pulse is delivered to a heart chamber during a cardiac cycle only after expiration of a defined escape interval during which no intrinsic beat by the chamber is detected. Escape intervals for ventricular pacing can be restarted by ventricular or atrial events, the latter allowing the pacing to track intrinsic atrial beats. Pre-excitation pacing for the purpose of arterial plaque stabilization as described above is preferably delivered in conjunction with a conventional synchronous pacing mode such as used for treating bradycardia. Excitatory stimulation pulses can then be delivered to selected sites during a cardiac cycle in order to both pace the heart in accordance with a bradycardia mode and provide pre-excitation of selected sites. Multiple excitatory pulses could also be delivered in demand mode to resynchronize the ventricles and provide a more synchronous cardiac contraction.

3. Stress Reduction Pacing for Stabilization of Arterial Plaque

Figure 2:
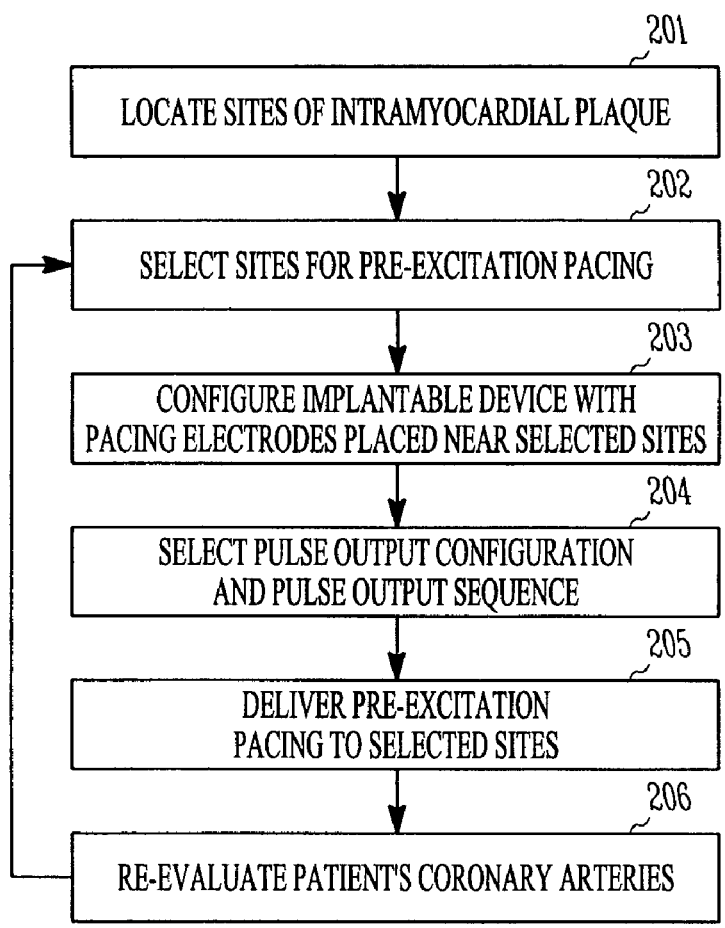
FIG. 2 illustrates an exemplary algorithm for implementing plaque stabilization therapy.

The device shown in FIG. 1 can be configured for stress reduction pacing such that one or more ventricular sites are paced in a manner that pre-excites at least one region of the ventricular myocardium that has been identified has containing an intra-myocardial portion of a coronary artery with atherosclerotic plaque. FIG. 2 illustrates the steps involved in an exemplary algorithm for implementing the procedure. At step 201, the patient's coronary arteries are imaged or otherwise analyzed to determine the location of intra-myocardial atherosclerotic plaque. Such analysis may be performed by, for example, X-ray angiography, magnetic resonance angiography, or computerized axial tomography. One or more corresponding ventricular pacing sites which are located in proximity to the intra-myocardial plaque sites can then be selected at step 202 for pre-excitation pacing. As described above, the object of such pre-excitation pacing is to mechanically unload the regions of the myocardium near the pacing sites during ventricular systole and thereby transmit less deforming forces to the intra-myocardial plaque. At step 203, an implantable cardiac rhythm management device with pacing functionality is configured to deliver the stress reduction pacing by disposing pacing electrodes near the selected pacing sites. For example, to pre-excite a right ventricular site, a pacing lead may be inserted intravenously into the right ventricle, while left ventricular sites may be reached by passing the pacing lead into the coronary sinus or a cardiac vein. Pacing electrodes may also be placed epicardially in certain instances. At step 204, the pulse output configuration and pulse output sequence are programmed into the device in order to pre-excite the selected myocardial regions. The pulse output configuration specifies a specific subset of the available electrodes to be used for delivering pacing pulses, and the pulse output sequence specifies the timing relations between the pulses. The pulse output configuration is defined by the controller selecting particular pacing channels for use in outputting pacing pulses and by selecting particular electrodes for use by the channel with switch matrix 70. The pulse output sequence defines the order of the pacing pulses delivered to the selected pacing electrodes and the time intervals between the pulses. Other pacing parameters are also specified such as the pacing mode (which may require configuration of other sensing/pacing channels such as for sensing and/or pacing the atria), pacing pulse energy, and pacing rate. After the device is operated with the selected pulse output sequence and configuration at step 205, the patient's coronary arteries may be re-evaluated at step 206. Appropriate modifications to the stress reduction pacing may then be made by repeating steps 202 through 205.

A cardiac rhythm management device may thus be operated with a pulse output configuration and pulse output sequence designed to reduce myocardial wall stress during systole of one or more regions which are in proximity to intra-myocardial atherosclerotic plaque. Such a pulse output configuration and pulse output sequence may also have the effect of synchronizing ventricular contractions and/or effecting reversal or prevention of ventricular remodeling. In cases where the optimum pulse output configuration and pulse output sequence for purposes of either resynchronization or reversal of remodeling is different from the optimum pulse output configuration and sequence for stabilizing intra-myocardial plaque, the device may be programmed to switch from one pulse output configuration and/or pulse output sequence to another in accordance with a measured variable such as exertion level or heart rate. For example, the device may be programmed to switch to a pulse output configuration/sequence optimal for stabilizing intra-myocardial plaque only at times when myocardial wall stress and coronary blood flow are expected to be high. Myocardial wall stress and coronary blood flow are high when the body's demand for cardiac output is high as indicated by an increased exertion level or, in a chronotropically competent patient, increased intrinsic heart rate. Patients with coronary artery disease are also prone to experience arrhythmias such ventricular tachycardia and fibrillation. A cardiac rhythm management device for delivering pacing therapy to stabilize intra-myocardial plaque would therefore preferably also monitor intrinsic cardiac activity for the presence of arrhythmias and deliver shock therapy as appropriate.

Although the invention has been described in conjunction with the foregoing specific embodiments, many alternatives, variations, and modifications will be apparent to those of ordinary skill in the art. Such alternatives, variations, and modifications are intended to fall within the scope of the following appended claims.

What is claimed is:

1. A method for treating coronary artery disease in a patient, comprising:
    placing a pacing electrode in proximity to a pacing site which is located near a site of atherosclerotic plaque within an intra-myocardial portion of the coronary artery; and,
    delivering pacing pulses to the pacing site in a manner which pre-excites the pacing site such that it contracts prior to other areas of the myocardium during a cardiac cycle.

2. The method of claim 1 wherein the pacing pulses are delivered to the pacing site in accordance with a demand pacing mode.

3. The method of claim 1 wherein the pacing pulses are delivered to the pacing site in a triggered pacing mode.

4. The method of claim 1 wherein the pacing electrode is disposed in the coronary sinus so as to pace a left ventricular pacing site.

5. The method of claim 1 wherein the pacing electrode is disposed in a cardiac vein so as to pace a left ventricular pacing site.

6. The method of claim 1 further comprising:
    placing a plurality of pacing electrodes in proximity to a plurality of pacing sites; and,
    delivering pacing pulses to one or more pacing sites according to a defined pulse output configuration and a defined pulse output sequence which pre-excites one or more pacing sites located near sites of atherosclerotic plaque relative to other areas of the myocardium during a cardiac cycle.

7. The method of claim 6 further comprising:
    detecting changes in the location of atherosclerotic plaque in the patient's coronary arteries; and modifying the delivery of pacing pulses so as to provide pre-excitation to pacing sites located near sites of atherosclerotic plaque.

8. The method of claim 7 further comprising pacing a plurality of pacing sites and modifying the delivery of pacing pulses by altering the pulse output sequence.

9. The method of claim 7 further comprising modifying the delivery of pacing pulses by altering the pulse output configuration.

10. The method of claim 6 further comprising delivering paces to a plurality of pacing sites in order to provide cardiac resynchronization therapy.

11. The method of claim 10 further comprising altering the pulse output configuration from one optimal for providing cardiac resynchronization therapy to one optimal for stabilizing intra-myocardial plaque in accordance with a measured variable.

12. The method of claim 11 wherein the measured variable is an exertion level.

13. The method of claim 11 wherein the measured variable is heart rate.

14. The method of claim 10 further comprising altering the pulse output sequence from one optimal for providing cardiac resynchronization therapy to one optimal for stabilizing intra-myocardial plaque in accordance with a measured variable.

15. The method of claim 14 wherein the measured variable is an exertion level.

16. The method of claim 14 wherein the measured variable is heart rate.

17. The method of claim 1 further comprising monitoring intrinsic cardiac activity for the presence of arrhythmias and delivering shock therapy as appropriate.

* * * * *

UNITED STATES PATENT AND TRADEMARK OFFICE
CERTIFICATE OF CORRECTION

| | | |
|---|---|---|
| PATENT NO. | : 7,158,824 B2 | Page 1 of 1 |
| APPLICATION NO. | : 10/664410 | |
| DATED | : January 2, 2007 | |
| INVENTOR(S) | : Girouard et al. | |

It is certified that error appears in the above-identified patent and that said Letters Patent is hereby corrected as shown below:

On the Title page, in Item (56), under "Other Publications", in column 2, line 3, delete "sever" and insert -- severe --, therefor.

In column 6, line 67, in Claim 7, after "and" insert -- , --.

Signed and Sealed this

Fifteenth Day of May, 2007

JON W. DUDAS
*Director of the United States Patent and Trademark Office*